United States Patent [19]

Fertig et al.

[11] Patent Number: 4,595,016

[45] Date of Patent: Jun. 17, 1986

[54] APNEA MONITOR

[75] Inventors: Glenn H. Fertig, Natrona Heights; Robert J. Wozniak, Belle Vernon, both of Pa.

[73] Assignee: Mine Safety Appliances Co., Pittsburgh, Pa.

[21] Appl. No.: 696,392

[22] Filed: Jan. 30, 1985

[51] Int. Cl.$^4$ .................................................. A61B 5/08

[52] U.S. Cl. ...................................... 128/719; 128/725

[58] Field of Search ....................... 128/224.22, 224.23, 128/203.14, 205.18, 205.19, 633, 664, 716, 717, 718, 719, 720; 250/343

[56] References Cited

U.S. PATENT DOCUMENTS

| | | | |
|---|---|---|---|
| 4,011,859 | 3/1977 | Frankenberger | 128/719 |
| 4,163,899 | 8/1979 | Burough | 250/343 |
| 4,350,166 | 9/1982 | Mobarry | 128/664 |
| 4,437,005 | 3/1984 | Ophoff et al. | 250/343 |

FOREIGN PATENT DOCUMENTS

| | | | |
|---|---|---|---|
| 2802770 | 7/1978 | Fed. Rep. of Germany | 128/716 |

*Primary Examiner*—Kyle L. Howell
*Assistant Examiner*—Daniel Haneiwich
*Attorney, Agent, or Firm*—Reed Smith Shaw & McClay

[57] ABSTRACT

An infrared fluid analyzer with an improved sensitivity and signal to noise ratio is provided. The device includes a capacitor microphone for detecting absorption of characteristic infrared wavelength lines by the sample and utilizes an electret material to electrically polarize the capacitive element in the microphone. The device is used to detect a stoppage of respiration in a person and thereby warn of the presence of an APNEA condition. The capacitor microphone generates a signal each time it detects an exhaled breath. When a timer senses an extended delay between signals, an alarm sounds indicating the presence of an APNEA condition.

3 Claims, 2 Drawing Figures

APNEA MONITOR

FIELD OF THE INVENTION

The invention relates to devices for detecting a patients respiration using infrared absorption techniques, and in particular to such devices that may be used for APNEA monitoring.

DISCUSSION OF THE TECHNICAL PROBLEM

APNEA in its classical sense means a weakness of respiration that results in a suspension of breathing. There are numerous methods used to monitor and warn of an APNEA condition. Most of these methods usually monitor the heartbeat in a patient. However, in many instances, a patient may stop breathing before the heart ceases to function. Thus it would be desirable to have earlier warnings of an APNEA condition by monitoring the patient's breathing. The present invention provides a means whereby a patient's breathing may be monitored by analyzing the prescence or absence of breath using infrared absorption techniques.

A device that uses infrared absorption techniques for APNEA monitoring is disclosed in Mobarry U.S. Pat. No. 4,350,166. The Mobarry patent provides a detector to measure the modulation of infrared by $CO_2$ that is found in the exhaled breath of an infant.

The device is designed to monitor the respiration of a baby by positioning the monitor over the baby's crib or bed. When the baby is placed in the bed, the device detects the difference in infrared radiation by absorbing $CO_2$ that is exhaled by the infant. There are however inherent drawbacks to Mobarry's design due to the positioning and size of the surveillance field that surrounds the baby.

Since the device detects ambient infrared produced by the infant's breath, movement or repositioning of the infant could create a variation of the infrared source. Also, since the device is not attached directly to the infant's nose or mouth, it detects concentrations of $CO_2$ in the surveillance field above and around the infant. Thus, even low level concentrations of $CO_2$ that may enter the field from surrounding ambient air would seriously interfere with the measurement of $CO_2$ concentration directly around the infant's head. As a result of these inherent drawbacks, it is unlikely that Mobary's device could provide a dependable and infallible APNEA monitoring system using the disclosed arrangement.

Conventional prior art infrared analyzers generally function to detect the presence and relative amounts of a particular material within a fluid sample to be analyzed, through analysis of the absorption by a sample of characteristic wavelength lines within the infrared spectrum. In theory, a source emits a constant beam of infrared radiation into a sample cell and a reference cell. A fluid sample within the sample cell absorbs characteristic wavelengths from the infrared spectrum that are not absorbed in the reference cell. Throughout this process, an interruptor rotates at a constant selected frequency such that windows permit alternate pulses to pass therethrough from the reference cell and the sample cell respectively.

A pneumatic detector then receives the alternating pulses and detects the difference in infrared signal levels therebetween through the effect of the infrared signals on the pressure of the gas within a compartment. The gas within the compartment is selected to be pressure responsive to the characteristic wavelengths absorbed in the sample cell, such that pressure changes occur in the compartment at the frequency at which the interrupter is operated. Finally, the pressure changes are converted into a corresponding electrical signal by a capacitive element formed by a diaphragm and a stator member. As the diaphragm moves in response to pressure changes in the compartment, an electrical signal is produced that corresponds to the changes in capacitance between the diaphragm and the stator. The electrical signal is amplified by an amplifier and is then displayed by a meter.

An infrared fluid analyzer, as disclosed in Fertig et. al. U.S. patent application Ser. No. 638,995, filed Aug. 9, 1984 operates in a manner similar to conventional analyzers. However, in the Fertig Application, a facility for substantially noise-free polarization of the diaphragm and stator is provided by comprising at least a portion of the diaphragm and/or stator of an electret material.

Some of the preceding inventions may be used to measure changes in carbon dioxide levels to detect APNEA. The following invention, however, discloses an apparatus that is much less expensive to manufacture, much simpler to design and fail-safe in nature.

SUMMARY OF THE INVENTION

The present invention provides an improved infrared fluid analyzer that may be used as an APNEA monitor. The monitor includes a pneumatic detector that substantially improves the signal to noise ratio and sensitivity of the system by polarizing the capacitive element thereof through the use of electret materials. In this manner the prior art resistor and source of EMF may be eliminated, thereby simplifying the detector circuitry while reducing noise levels.

Further, the present invention provides a means whereby the sample gas modulates an infrared beam which causes a signal to be generated. Thus the invention completely eliminates the need for an optical interrupter.

DESCRIPTION OF PREFERRED EMBODIMENT

Figure 1:
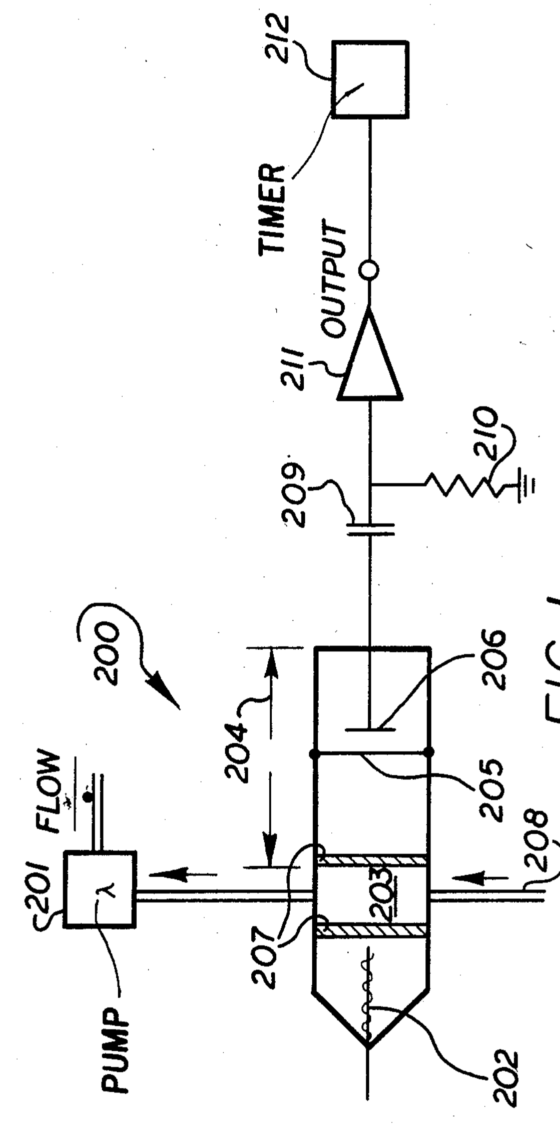
FIG. 1 is a schematic view of an APNEA Monitor in accordance with the present invention.

With reference to FIG. 1, an APNEA monitor 200 according to the present invention is schematically illustrated. The monitor 200 incorporates a number of the elements comprising conventional infrared fluid analyzers, however, to be noted initially is the complete elimination of an optical interrupter. The interrupter is replaced in the present invention with sample pump 201.

The monitor 200 comprises of a source of infrared energy 202. The energy from the source is directed through a sample cell 203, that contains windows 207, and into an infrared detector 204. The detector 204 may be of any type described in the previous prior art disclosures.

A preferred form of the detector 204 is a pneumatic means that consists of a diaphram 205 that may be comprised of an electret material and a stator 206. Together, the electret material and stator 206 form a capacitor microphone. This microphone assembly is positioned inside the infrared detector 204. The infrared detector 204 is an hermetically sealed chamber that contains a sample of the type of gas that is to be detected.

A means 208 of acquiring a sample of exhaled $CO_2$ from the patient is attached to the patient's nose or mouth. A sample of exhaled breath is then drawn through the acquisition means 208 and into the sample cell 203 by pump means 201. The breath is drawn through the sample cell 203 in a direction as indicated in FIG. 1.

As the sample of exhaled breath is drawn through the sample cell 203, infrared energy is absorbed, and a pressure difference is produced in detector 204. Each time a difference in pressure occurs in 203, the flucuation in pressure moves diaphram 205. When diaphram 205 moves, a signal is generated from the capacitor microphone. This signal is then differentiated by capacitor 209 and resistor 210. The differentiated signal is then amplified by amplifier 211. The output from the amplifier 211 is used to activate a timing means 212 such as a watchdog timer. A watchdog timer is a device, well known in the field, that senses when an event does not occur and then immediately sounds an alarm. In the present invention the event which the timer 212 senses is the output signal from the amplifier 211.

Figure 1A:
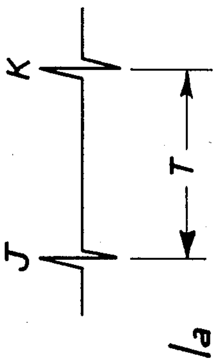
FIG. 1*a* is a diagram illustrating signals generated by a patient's breath on a time axis.

With reference to FIG. 1A, the watchdog timer 212 detects the amount of time T between signals J and K. Each time the patient takes a breath, a signal is generated. If the time T between breaths exceeds a preset amount, an alarm sounds indicating an APNEA alert. The breathing rate alarm is adjustable and may be varied from patient to patient. Generally, the alarm will be set to sound if the interval between breaths exceeds 10 to 40 seconds.

The present invention is unique in that it uses the exhaled carbon dioxide in the breath to modulate the infrared beam. The resulting modulation of the beam causes a signal to be generated, thereby completely eliminating the need for an optical interrupter.

Of course the present invention is not to be limited to the specific preferred embodiments described above, but rather by the claims which follow.

What is claimed is:

1. An apnea monitor comprising a. Source means for producing an unmodulated beam of infrared radiation;

b. A sample cell in which fluid to be analyzed is contained, said sample being positioned in said unmodulated beam of radiation;

c. pneumatic detector means positioned to receive infrared radiation after passage through said sample cell;

d. means for drawing or pumping exhaled breath through said sample cell;

e. means for detecting the time between signals generated by said pneumatic detector; and f. alarm means that is responsive to a significant delay between said signals.

2. An apnea monitor as set forth in claim 1, wherein said infrared detector comprises a fluid chamber having a fluid responsive to changes in infrared radiation; a diaphram in communication with said fluid to move in response thereto; a stator means spaced from and electrically connected to said diaphram; and an electret polarizer.

3. An apnea monitor as set forth in claim 2, wherein said electret is part of said diaphram or stator.

* * * * *